(12) United States Patent
Eppler

(10) Patent No.: US 6,819,739 B2
(45) Date of Patent: Nov. 16, 2004

(54) METHOD AND APPARATUS FOR CALIBRATING AN X-RAY LAMINOGRAPHY IMAGING SYSTEM

(75) Inventor: Barry Eppler, Loveland, CO (US)

(73) Assignee: Agilent Technologies, Inc., Palo Alto, CA (US)

(*) Notice: Subject to any disclaimer, the term of this patent is extended or adjusted under 35 U.S.C. 154(b) by 49 days.

(21) Appl. No.: 10/306,681

(22) Filed: Nov. 27, 2002

(65) Prior Publication Data

US 2004/0101110 A1 May 27, 2004

(51) Int. Cl.[7] ............................................. G01N 23/00
(52) U.S. Cl. ........................ 378/21; 378/25; 378/207
(58) Field of Search .............................. 378/207, 21–27

(56) References Cited

U.S. PATENT DOCUMENTS 4,926,452 A    5/1990  Baker et al.
5,097,492 A *  3/1992  Baker et al. .................. 378/22
5,259,012 A   11/1993  Baker et al.
6,201,850 B1   3/2001  Heumann

* cited by examiner

Primary Examiner—Craig E. Church
Assistant Examiner—Jurie Yun

(57) ABSTRACT

An x-ray laminography imaging system and an apparatus and method for calibrating the system. The x-ray laminography imaging system utilizes a stationary x-ray source and generates a moving pattern of x-ray spots on a target anode synchronously with rotation of an x-ray detector to reduce or eliminate the need to move an object being imaged. The present invention provides an apparatus and a method for calibrating the system based in part on empirical data gathered during physical calibration and in part on data analytically derived from the empirical data. Because calibration of the system can be performed in great part analytically rather than relying entirely on empirically generated data, the calibration process can be performed very quickly.

34 Claims, 10 Drawing Sheets

METHOD AND APPARATUS FOR CALIBRATING AN X-RAY LAMINOGRAPHY IMAGING SYSTEM

TECHNICAL FIELD OF THE INVENTION

The present invention relates to x-ray imaging and, more particularly, to calibrating an x-ray laminography imaging system that utilizes a stationary x-ray source and generates a moving pattern of x-ray spots on a target to reduce or eliminate the need to move the object being imaged.

BACKGROUND OF THE INVENTION

Laminography techniques are widely used to produce cross-section images of selected planes within objects. Conventional laminography requires a coordinated motion of any two of three main components comprising a laminography system (i.e., a radiation source, an object being inspected, and a detector). The coordinated motion of the two components can be in any of a variety of patterns, including linear, circular, elliptical and random patterns. Regardless of the pattern of coordinated motion selected, the configuration of the source, object and detector is such that any point in the object plane (i.e., the focal plane within the object) is always projected to the same point in the image plane (i.e., the plane of the detector), and any point outside the object plane is projected to a plurality of points in the image plane during a cycle of the pattern motion. In this manner, a cross-section image of the desired plane within the object is formed on the detector. The images of other planes within the object experience movement with respect to the detector thus creating a blur, i.e. background, on the detector upon which is superimposed the sharp cross-section image of the focal plane within the object. This technique results in sharp images of the desired object focal plane. Although any pattern of coordinated motion can be used, circular patterns are generally preferred because they are more easily produced.

The laminography techniques described above are currently used in a wide range of applications including medical and industrial X-ray imaging. Laminography is particularly well suited for inspecting objects that comprise several layers, with each layer having distinguishable features. However, laminography systems that produce such cross-sectional images typically experience shortcomings in resolution and/or speed of inspection, thus accounting for its rare implementation. These shortcomings are frequently due to the difficulties in achieving high speed coordinated motion of the source and detector to a degree of precision sufficient to produce a high resolution cross-section image.

In a laminography system having a field of view that is smaller than the object being inspected, it may be necessary to move the object around within the field of view to obtain multiple laminographs which, when pieced together, cover the entire object. Movement of the object is frequently achieved by supporting the object on a mechanical handling system, such as an X, Y, Z positioning table. The table is then moved to bring the desired portions of the object into the field of view. Movement in the X and Y directions locates the area to be examined, while movement in the Z directions moves the object up and down to select the plane within the object where the image is to be taken. While this method effectively enables various areas and planes of the object to be viewed, there are inherent limitations associated with the speed and accuracy of such mechanical motions. These constraints effectively act to increase cycle time, thereby reducing the rates at which inspection can occur. Furthermore, these mechanical motions produce vibrations which tend to reduce the system resolution and accuracy.

In order to reduce or eliminate the need to move the object, and the problems associated therewith, an off-axis laminography system has been invented, which is disclosed in U.S. Pat. No. 5,259,012 (the '012 patent) and which is incorporated herein by reference in its entirety. The '012 patent discloses a laminography system in which off-axis scanning circles can be used to enable multiple locations on an object to be sequentially imaged without requiring mechanical movement of the object. The phrase "off-axis" refers to placing the center of the scan circle in a position that is not concentric with the optical axis of the imaging system. In the imaging system disclosed in the '012 patent, x-rays are produced when highly accelerated electrons impinge on a metal target. The point where the x-rays are produced is commonly referred to as the "spot". The spot can be steered across the target by electronically controlled deflection coils which act on the electron beam. Moving the scan patterns (i.e., the pattern of spots) produces laminographs at desired X, Y coordinate locations with various Z planes and generally reduces or eliminates the need to mechanically move the object.

The '012 patent discloses an x-ray source that includes an electron gun that emits an electron beam. The electron beam is incident upon a flat target anode (hereinafter referred to as "the target"). Focus and deflection coils direct the electron beam to specific locations on the target to form the aforementioned circular electron beam patterns on the surface of the target. When the electrons are slowed down or stopped in the target, Bremsstrahlung x-rays are generated. Since the electron beam describes a moving circular pattern on the target, the source of Bremsstrahlung x-rays also describes a moving circular pattern coincident with the electron beam pattern. In one embodiment of the '012 patent, steering signals applied to the deflection coils cause the electron beam spot to rotate in a predetermined path in coordination with a similar path of the detector. In an embodiment, a digital look-up-table (LUT) sends digital signals to the deflection coils that cause the beam spot to follow the circular motion of the electron beam on the target. In the latter case, digital addresses corresponding to the location of the x-ray detector along the circle traced by the detector are sent from the detector to the LUT. The LUT then sends deflection signals corresponding to specific detector positions to the electron beam deflection coils. The values of the deflection signals are calibrated to cause the x-ray source to trace a circular pattern upon the target that is precisely coordinated with the motion of the detector.

Current laminography calibration techniques trace the circular patterns on the target and gather empirical data for each circular pattern. The empirical data for each circular pattern is then processed to generate the LUT values needed to reproduce the circular pattern at run time. This type of calibration technique is suitable for on-axis laminography because the number of circular scan patterns is not too great (e.g., N scan circles for N different magnifications, where N=4 for typical existing implementations). Therefore, calibrating the system to obtain the appropriate LUT values may take, for example, one to four hours (depending on the level of magnification). However, when off-axis laminography is employed, the number of scan circles that must be generated to cover the object area of interest increases significantly due to the number of different off-axis positions. Thus, depending on the size of the scan circles that are desired and the target area available, the number of scan circles needed to image the object may increase significantly when performing off-axis laminography. If the aforementioned calibration technique is employed for an off-axis laminography system, these numbers suggest that multiple days may be required to calibrate the system for off-axis imaging at multiple magnifications. Calibration times of this length are generally unacceptable to users.

Accordingly, a need exists for a calibration method and apparatus that are suitable for use with on-axis and off-axis laminography and that enable calibration to be performed in a relatively short amount of time.

SUMMARY OF THE INVENTION

The present invention provides an x-ray laminography imaging system that utilizes a stationary x-ray source and generates a moving pattern of x-ray spots on a target anode synchronously with rotation of an x-ray detector to eliminate the need to move an object being imaged. The present invention provides an apparatus and a method for calibrating the system based in part on empirical data gathered during physical calibration and in part on data analytically derived from the empirical data. Because calibration of the system can be performed in great part analytically rather than relying entirely on empirically generated data, the calibration process can be performed very quickly.

The apparatus comprises first logic, second logic and third logic, which preferably correspond to a processor configured to execute a calibration algorithm. The first logic is configured to gather empirical calibration data generated during physical calibration of the system during which a stationary x-ray source generates a moving pattern of x-ray spots on a target anode synchronously with rotation of an x-ray detector. The empirical data corresponds to offsets to locations at which the x-ray spots should be formed on the target anode. The second logic is configured to analytically derive calibration data from the empirical data, preferably by interpolation. The third logic is configured to calibrate the system using the empirical data and the analytically-derived calibration data.

The system comprises a controllable deflection yoke that receives control signals from a processor. The controllable deflection yoke controls particular locations on the target anode upon which x-rays projected by an x-ray source along a Z-axis impinge in accordance with the control signals received. The target anode is oriented substantially parallel to a plane that is substantially orthogonal to the Z-axis. The x-rays projected along the Z-axis impinge at particular locations on the target anode that are dependent on control signals received by the controllable deflection yoke. The x-rays directed onto the target anode form substantially circular x-ray spot patterns on the target anode, with each x-ray spot pattern being produced by movement of an x-ray spot in a substantially circular pattern. Each x-ray spot corresponds to a beam of x-rays impinging on a particular location on the target anode. The control signals cause the deflection yoke to form at least one substantially circular on-axis x-ray spot pattern on the target anode about the Z-axis and at least one substantially circular off-axis x-ray spot pattern on the target anode about an axis that is substantially parallel to the Z-axis. The processor determines the control signals needed to be delivered to the deflection yoke to cause the off-axis x-ray spot pattern to be formed based on data associated with the on-axis x-ray spot pattern.

The determination by the processor of where on the target anode the x-ray spots of the off-axis x-ray patterns are to be formed is analytically made using the empirically-generated offset on-axis x-ray patterns. From a relatively small number of empirically-generated offset on-axis patterns, a large number of off-axis x-ray patterns can be generated and used to calibrate the system.

The method of the present invention comprises the following steps: determining control signals needed to be delivered to a deflection yoke to cause at least one substantially circular on-axis x-ray spot pattern to be formed on a target anode about a Z-axis to simulate rotation of an x-ray source; processing data gathered through calibration of the system as a rotating x-ray detector is synchronized to the motion of the x-ray spots about the Z-axis that form the on-axis x-ray spot pattern to determine offsets to the X, Y coordinates of the x-ray spots of the pattern on the target anode; using the offsets to offset the X, Y coordinates of the x-ray spots of the on-axis x-ray spot pattern as they x-ray spot pattern is being formed on the target anode, thereby causing an offset on-axis x-ray spot pattern to be formed on the target anode about the Z-axis; and using the x-ray spot offsets associated with the on-axis x-ray spot pattern to determine a substantially circular off-axis x-ray spot pattern to be formed on the target anode about an axis that is substantially parallel to the Z-axis.

These and other features and advantages of the present invention will become apparent from the following description, drawings and claims.

DETAILED DESCRIPTION OF THE PREFERRED EMBODIMENTS

A laminography system that is suitable for use with the present invention is disclosed in the aforementioned '012 patent, which is assigned to the assignee of the present application and which is incorporated herein by reference. For convenience, the system described in the '012 patent and the manner in which it operates is described below with reference to FIGS. 1–4B. It should be noted, however, that the present invention is not limited to use with any particular type of laminography system or to any specifically configured laminography system. The laminography system described below is merely an example of one system with which the present invention may be used. Also, although the laminography system described herein performs off-axis scanning, the present invention is equally applicable to on-axis scanning. However, because a greater need exists for the employment of the present invention for off-axis scanning due to the greater computational intensity of off-axis scanning compared to on-axis scanning, the present invention will only be described with reference to its use with off-axis scanning. Those skilled in the art will understand, in view of this disclosure, the manner in which the present invention can be used to calibrate an on-axis scanning system.

Figure 1:
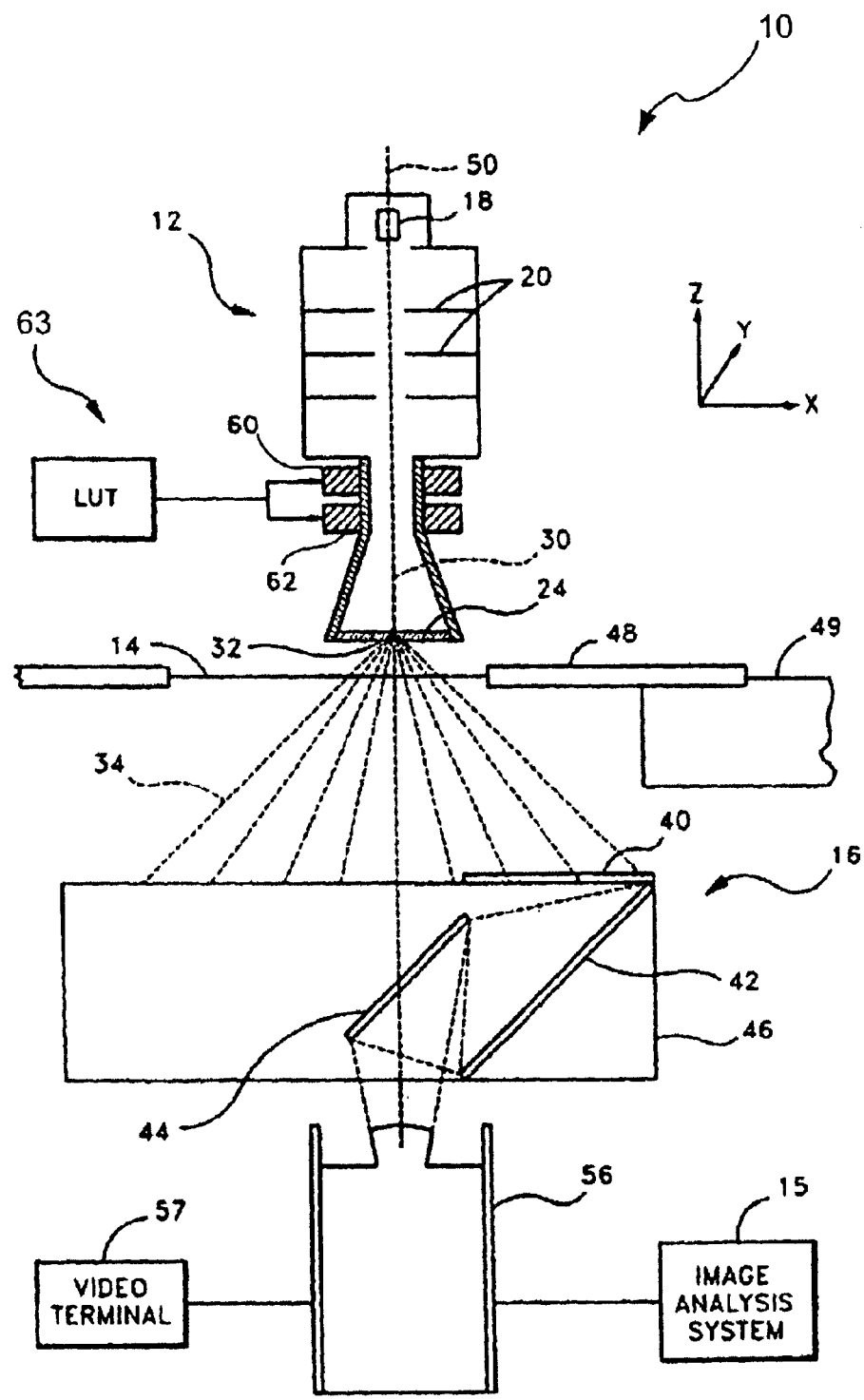
FIG. 1 is a schematic view of a laminography system in accordance with an embodiment of the present invention.

FIG. 1 illustrates a schematic diagram of a laminography system 10 in accordance with an embodiment of the present invention. The system 10 comprises a source of x-rays 12 positioned above an object 14 to be imaged, and a rotating x-ray detector 16, positioned below the object 14 and opposite the x-ray source 12. The object 14 may be, for example, a circuit board, a manufactured item such as, for example, an aircraft part, a portion of a human body, etc.

The system 10 is symmetrical about a Z-axis 50. The system 10 acquires X, Y plane cross-sectional images of the object 14 under inspection using multipath laminography geometries, which enable multiple locations of the object 14 to be sequentially imaged without requiring mechanical movement of the object 14. In other words, off-axis (i.e., not about the axis 50, but about an axis parallel to axis 50) scanning patterns are used to image the object over different regions of the object in the X, Y plane. The manner in which different regions of the object 14 in different Z-planes are imaged will be discussed below in detail with reference to FIGS. 4A and 4B.

The laminography system 10 may be interfaced with an analysis system 15 that automatically evaluates the cross-sectional image generated by the system 10 and provides a report to a user indicating the results of the evaluation. The source 12 is positioned adjacent the object 14, and comprises an electron gun 18, a set of electrodes 20 for electron beam acceleration and focus, a focus coil 60, a steering yoke or deflection coil 62, and a substantially flat target anode 24. An electron beam 30 emitted from the electron gun 18 along the Z-axis 50 is incident upon the target anode 24 and causes an x-ray spot 32 to be produced, which serves as an approximate point source of x-rays 34. The x-rays 34 emanate from a point on the target anode 24 where the electron beam 30 impinges upon the target anode 24. As described below in detail, at least a portion of these x-rays pass through various regions of the object 14 and impinge on the detector 16.

The object 14 is typically mounted on a platform 48 which may be affixed to, for example, a granite table 49, so as to provide a rigid, vibration-free platform for structurally integrating the functional elements of the system 10, including the x-ray source 12 and the turntable 46. It is also possible that the platform 48 comprises a positioning table that is capable of moving the object 14 along three mutually perpendicular axes, labeled X, Y, and Z in FIG. 1. As stated above, with off-axis scanning, it generally is not necessary to physically move the object. However, it may be desirable to move the object to some degree to improve image quality. At any rate, with off-axis scanning, it is not necessary to move the object anywhere near as much as with on-axis scanning.

The rotating x-ray detector 16 comprises a fluorescent screen 40, a first mirror 42, a second mirror 44, and a turntable 46. The turntable 46 is positioned adjacent the object 14 on the side of the object 14 opposite the x-ray source 12. A camera 56 is positioned opposite the mirror 44 for capturing images reflected into the mirrors 42, 44 from the fluorescent screen 40. The camera 56 may comprise a low light level, closed circuit television camera that produces a video image of the x-ray image formed on the fluorescent screen 40. The camera 56 may be, for example, connected to a video terminal 57 so that a user may observe the image appearing on the detector 40. The camera 56 may also be connected to the image analysis system 15.

In operation, x-rays 34 produced by the x-ray source 12 illuminate and penetrate regions of the object 14 and are intercepted by the screen 40 of detector 16. Synchronous rotation of the x-ray source 12 and detector 16 about the axis 50 causes an x-ray image of a plane 52 (FIG. 2) within the object 14 to be formed on the detector 16. Although the axis of rotation 50 illustrated in FIG. 1 is the common axis of rotation for both the source 12 and detector 16, as stated above, these axes of rotation are not collinear in an off-axis system. Rather, these axis are parallel to one another, as will be described below with reference to FIGS. 3A–4B.

Figure 2:
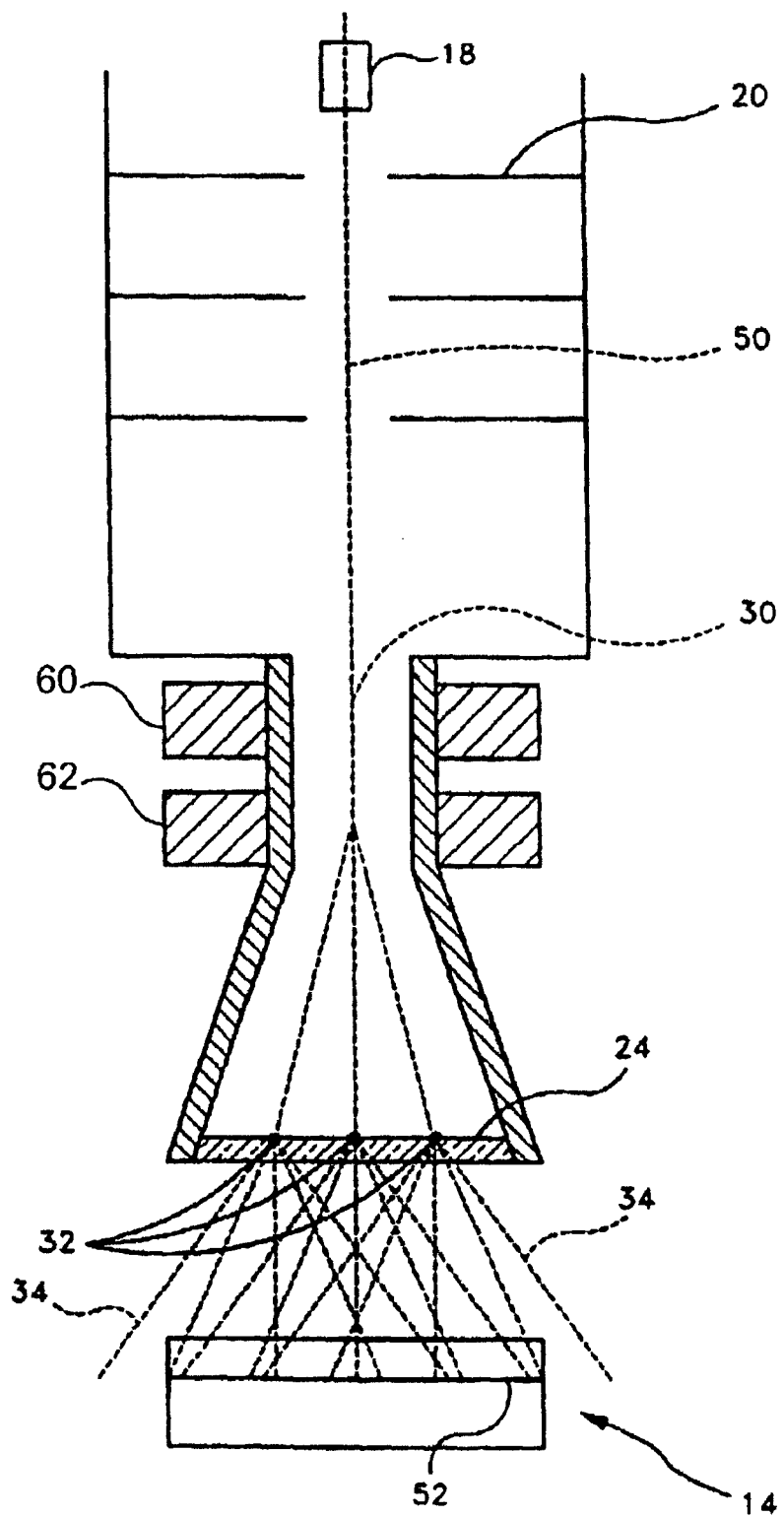
FIG. 2 is a schematic view of the laminography system shown in FIG. 1 and a region in the X, Y plane of the object being imaged.

The electron beam 30 is emitted from the electron gun 18 and travels in a region between the electrodes 20 and steering coils 60, 62. FIG. 2 is a schematic view of the laminography system 10 shown in FIG. 1 and a region in the X, Y plane 52 of the object 14 that is being imaged. As shown in FIG. 2, the electrodes 20 and coils 60, 62 produce electromagnetic fields that interact with the electron beam 30 to focus and direct the beam 30 onto the target anode 24, thereby forming an electron beam spot 32 on the target anode (hereinafter "the target") 24 from which x-rays are emitted. The size of the electron beam spot 32 on the target 24 may be, for example, on the order of 0.02 to 10 microns in diameter. The steering coils 60, 62 enable the x-ray source 12 to provide x-rays 34 from the x-ray spots 32 such that the locations of the spots 32 move in a desired pattern around the target 24. It is the creation of the desired x-ray spot patterns on the target 32 that eliminate or reduce the need to physically move the object 14 to obtain images of different regions of the object 14 in the X, Y plane in different Z-planes.

Preferably, the steering coils 60, 62 are separate X and Y electromagnetic deflection coils that deflect the electron beam 30 discharged from the electron gun 18 in the X and Y directions, respectively. Electrical current flowing in the steering yoke 62 creates a magnetic field that interacts with the electron beam 30, thereby causing the beam 30 to be deflected. The configuration of the x-ray spot pattern on the target 24 depends on the where the beam 30 strikes the target 24, which depends on the manner in which the beam 30 is steered. It should be noted that electrostatic deflection techniques could also be used to deflect the electron beam 30.

Preferably, a LUT 63 (FIG. 1) outputs voltage signals that are applied to the X and Y deflection coils 60, 62 to cause the electron beam spot 32 (FIG. 2) to rotate, thus producing a circular spot pattern on the surface of the target anode 24. In accordance with one embodiment, the LUT 63 provides the output voltages in response to address signals received by the LUT 63 from a master computer (not shown), which may be included within the image analysis system 15. The values stored in the LUT 63 are predetermined using a calibration technique that correlates the position of the turntable 46 (i.e., the rotational position of the detector 16 and the position of the x-ray beam spot 32. Preferably, the values stored in the LUT 63 correspond to the rotational positions of the turntable 46. The turntable outputs electrical signals as it rotates that correspond to its rotational position. Once calibration has been performed using these electrical signals, the calibrated electrical signals are converted into digital values and stored the LUT 63 at appropriate addresses. The preferred method for performing the calibration technique is described below in detail with reference to FIG. 5.

Because the output voltages stored in the LUT 63 are in digital form, then as the digital values are read out of the LUT 63, they are converted into analog values by a digital-to-analog converter (not shown), amplified by an amplifier (not shown) and applied to the X and Y deflection coils 60 and 62, respectively, which causes the electron beam spot 32 to rotate in coordination with the rotation of the turntable 46. The rotation of the electron beam spot 32 produces a circular spot pattern on the surface of the target anode 24.

As stated above, the laminographic imaging system 10 enables various regions of the object 14 to be imaged with little or no physical movement of the object 14 or of the supporting table 48. In accordance with the present invention, desired regions of the object 14 are brought within the field of view (FOV) of the system 10 by moving the location of the FOV. This is accomplished by moving the location of the pattern traced by the x-ray beam spot 32 on the target 24. In this manner, various portions of the object 14 are brought within the FOV of the system 10 and images are produced of the portions of the object 14 as they coincide with the FOV. In accordance with the present invention, the voltages applied to the X and Y deflection coils 60, 62 are varied in order to produce rotating x-ray beam paths of distinct radii and having distinct x, y locations on the target 24.

Figure 3A:
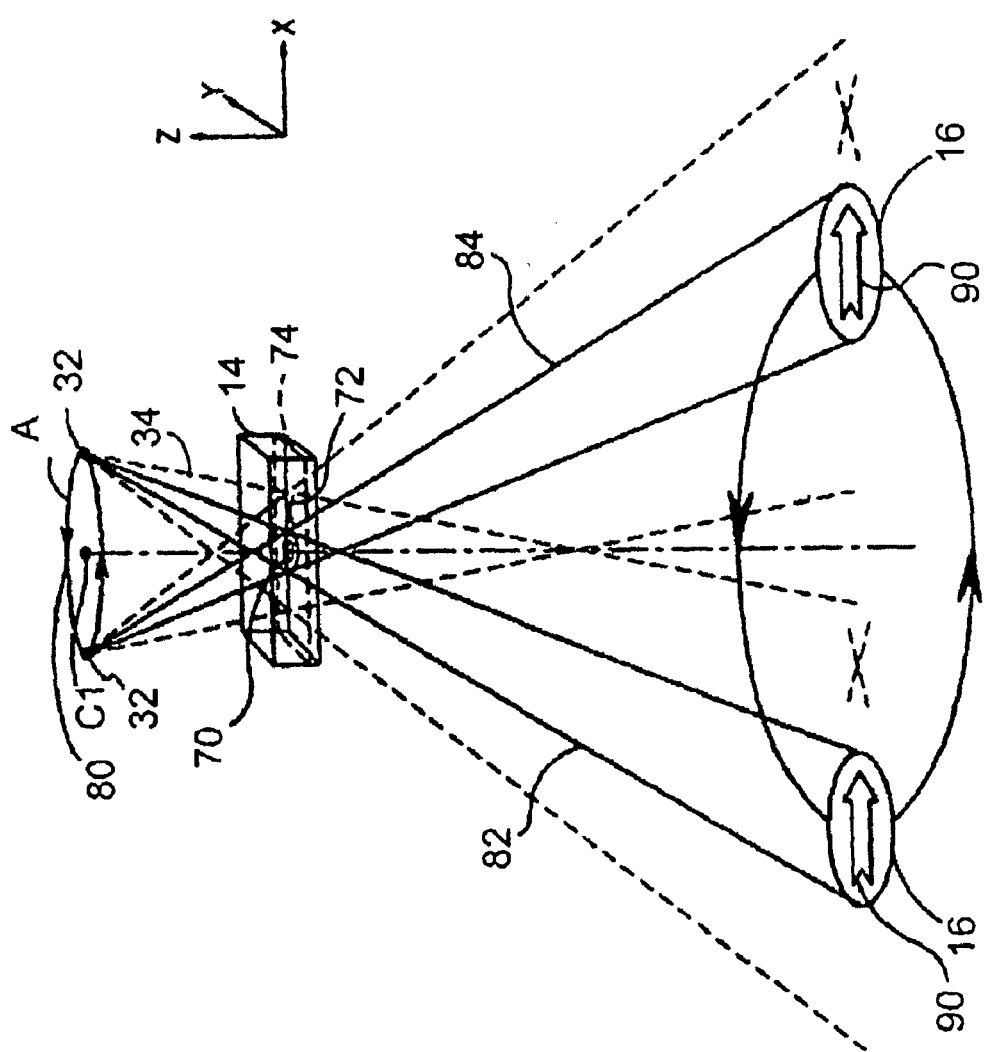
FIGS. 3A and 3B illustrate the manner in which the laminography system shown in FIG. 1 is utilized to produce an X-Y axis shift of the image region within the object.

FIG. 3A illustrates the laminography geometry and technique used to image different x, y regions of the object by electronically moving the center of rotation of the rotating x-ray source 12 on the target 24. The rotating spot 32 of x-rays 34 formed in the manner described above is positioned above the object 14 to be imaged. For purposes of illustrating the operation of the invention, the object 14 contains the patterns of an arrow 70 and a cross 72 located within different regions of an internal plane 74 of the object. As previously described, signals from the LUT 63 can be applied to the X and Y deflection coils 60, 62 (FIG. 2) so as to cause the x-ray spot 32 to trace a circular path on the target anode 24.

In the position labeled A in FIG. 3A, a scan circle 80 having a center C1 is produced, which emits x-rays 34 that are incident upon the object 14. As the x-ray spot 32 and detector 16 rotate in synchronization, as described above, the x-rays 34 are emitted in diverging beams at each point along the scan circle 80, forming a family of cones or conical regions, with each cone having an apex defined by the x-ray spot 32 and a base defined by the detector assembly 16. Two cones 82 and 84 defined by the x-ray spot 32 and detector 16 at two different locations along the circular path of the scan circle 80 are shown in FIG. 3A. The intersection of these conical regions around a complete rotation of the x-ray spot 32 and detector 16 defines a set of points within respective FOVs. Thus, the portion of the object plane that coincides with the FOV at a particular rotational position is imaged by the detector 16.

As illustrated in FIG. 3A, the intersection of the cones 82 and 84 produced by the rotating X-ray spot 32 and detector 16 is substantially centered about the arrow pattern 70 in the internal plane 74 of the object 14. In this manner, the rotating x-ray spot 32 and detector 16 produce a distinct image 90 of the arrow upon the detector 16. Because the cross pattern 72 lies outside the FOV defined by the intersecting cones 82 and 84, when the path 80 is traced by the electron beam 30, the image of the cross pattern 72 does not fall on the detector 16 at any time during the rotation of the detector 16 and thus, does not form an image on the detector 16.

Figure 3B:
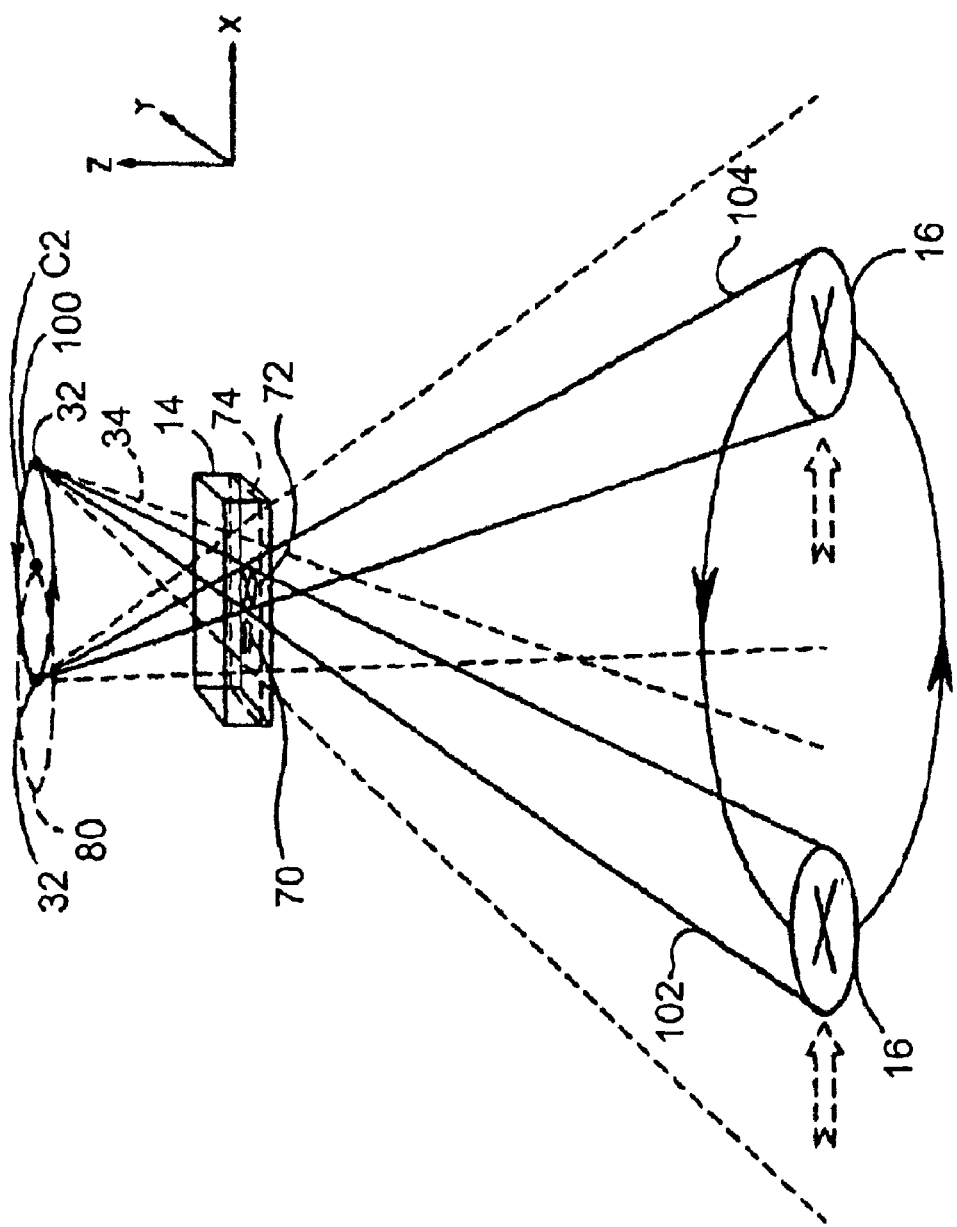

Application of an offset voltage to the X and/or Y deflection coils 60 and/or 62 acts to shift the path traced by the x-ray spot 32, as shown in FIG. 3B, such that a scan circle 100 having a center C2 is traced by the x-ray spot 32 on the target 24. As the x-ray spot 32 rotates about the circle 100, a second family of cones, represented by the two cones 102 and 104 in FIG. 3B, intersects the object plane 74 and defines a field of view substantially centered about the cross pattern 72. Thus, a new field of view, which is linearly displaced from the original field of view shown in FIG. 3A, is defined when the path traced by the x-ray spot 32 has its center of rotation shifted in the X and/or Y directions from center of rotation C1 to center of rotation C2. The circle 100 is off-axis, whereas the circle 80 is on-axis.

The arrow pattern 70 now lies outside the field of view in the object plane 74 such that, as the x-ray spot 32 and detector 16 rotate, a cross-sectional image of the cross pattern 72 is produced on the detector 16, and the image of the arrow 70 does not appear. The amplitude of the offset applied to the deflection coils 60, 62 is proportional to the distance and direction the path traced by the x-ray spot 32 is shifted, i.e., the distance and direction that the center of the scan circle is shifted depends on the amplitude of the offset signal applied to X, Y deflection coils 60, 62. Thus, the laminography geometry of the present invention enables different regions of the object 14 to be viewed and imaged upon the detector 16 without any physical movement of the source 12 or object 14. This reduces or eliminates vibrations or other adverse effects resulting from mechanical movement of the system components, which increases the speed and accuracy of the system 10.

It should be noted that shifting the position of the path traced by the x-ray spot 32 results in a change in the distance of the path followed by the electron beam 30. In other words, the distance from the cathode 18 to the surface of the target 24 changes each time the position of the x-ray spot 32 is shifted. This results in a change in the focal length of the electron beam 30, and dynamic focusing of the beam 30 should be brought about in order to maintain a sharp focal point of the electrons within the beam 30 at the surface of the target 24. The present invention changes the voltage applied to the focusing coil that is appropriate to maintain the focal point of the beam 30 at the surface of the anode 24.

Figure 4A:
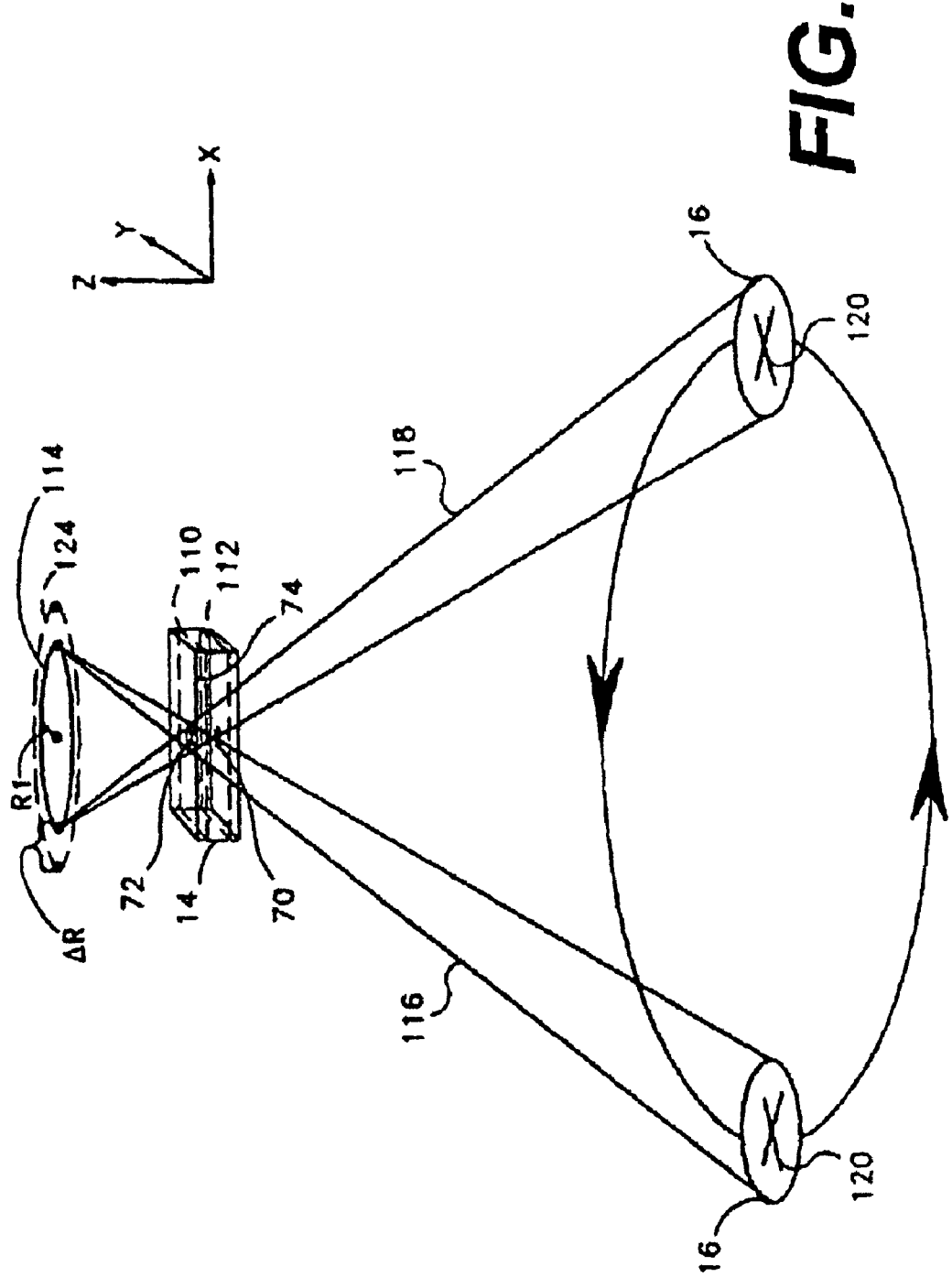
FIGS. 4A and 4B illustrate the manner in which the laminography system shown in FIG. 1 is utilized to produce a Z-axis shift of the imaged region of the object plane within the object.
Figure 4B:
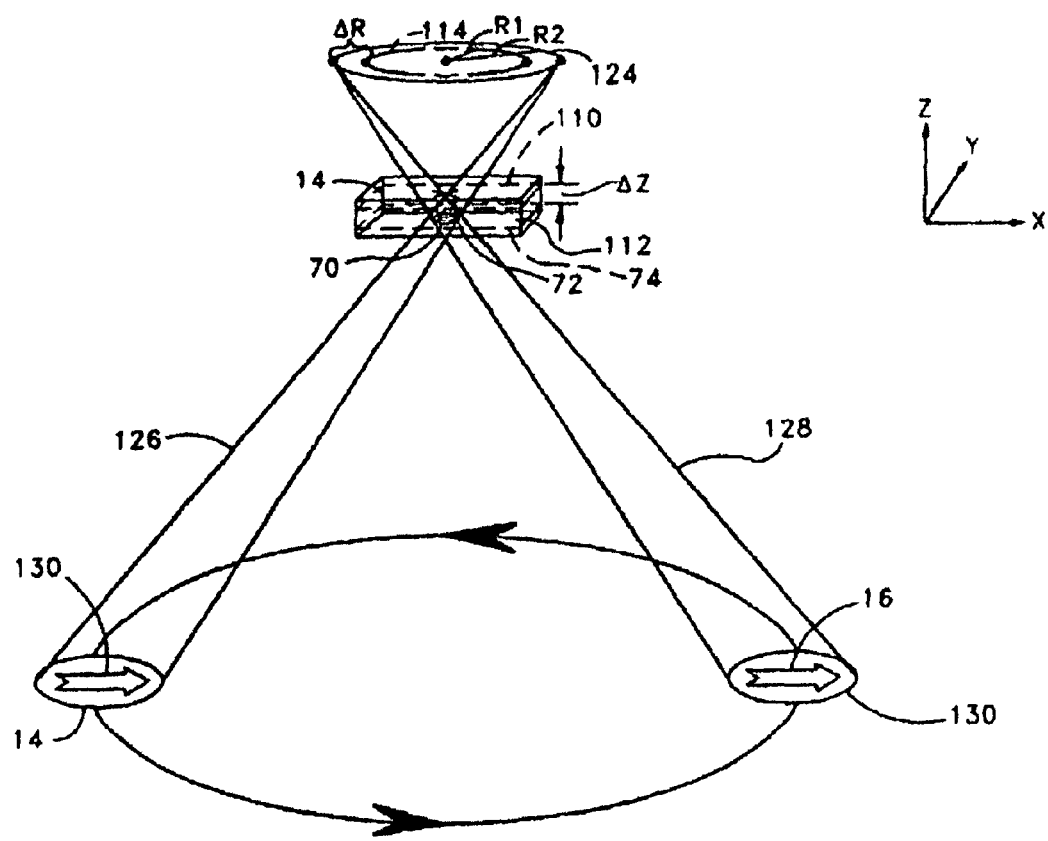

FIGS. 4A and 4B illustrate the manner in which the laminography system 10 shown in FIG. 1 is utilized to produce a Z-axis shift of the imaged region of the object plane within the object. FIG. 4A illustrates an object 14 having the patterns of an arrow 70 and a cross 72 located in a plane of the object 14. The cross pattern 72 is located in a first plane 110 and the arrow pattern 70 is located in a second plane 112. The first plane 110 lies above and is parallel to the second plane 112. The x-ray spot 32 traces a scan circle 114 having a radius R1, which defines a family of cones including cones 116 and 118. The intersection of the cones around the circle 114, including cones 116 and 118, forms an image region substantially centered about the cross pattern 72, such that the first plane 110 is defined as the object plane 74. As the x-ray spot 32 and detector 16 rotate in synchronization, a distinct image 120 of the cross pattern 72 is produced on the surface of the detector 16. The image of the arrow 70, which lies in the second plane 112 and is outside the object plane 74 defined by the cones 116 and 118, is not stationary on the detector 16 during the entire rotation of the detector 16 and thus, appears blurred.

FIG. 4B demonstrates that by equally adjusting the gain of the voltages output from the LUT 63 to both deflection coils 60, 62, the amplitudes of the sine and cosine signals are changed. Changing the amplitude of the sine and/or cosine signals applied to the deflection coils 60 and 62 causes the radius of the scan circle traced by the x-ray spot 32 to vary, which causes images of regions within distinct planes in the object 14 to be produced. With this gain adjustment, the scan circle 114 is increased in radius by a value Δr to a radius R2, thereby forming a scan circle 124 defining a second family of cones including the cones 126 and 128. Because of the larger radius R2 of the second scan circle 124, the set of points defined by the intersection of the second family of cones, including cones 126 and 128, is displaced in the negative Z-direction relative to the region imaged when the x-ray source 32 follows the path 114 (FIG. 4A). Thus, the object plane 74 is lowered by an amount Δz to the second plane 112, and the image region is substantially centered about the arrow pattern 70.

As the x-ray spot 32 and detector 16 rotate, a distinct image 130 of the arrow pattern 70 is produced on the detector 16, whereas the image of the cross pattern 72 lying outside the object plane 74 appears blurred. The amplitude of the gain adjustment made to the voltages applied to the deflection coils 60, 62 is proportional to the direction and amount of the shift Δz in the object plane 74. For example, a large increase in the gain would result in a relatively large movement of the image plane 74 in the downward (i.e., negative Z) direction, while a small decrease in the gain would result in a relatively small movement of the image plane 74 in the upward (i.e., positive Z) direction. In this manner, the geometry utilized in the laminographic system of the present invention further allows various planes in the object 14 to be imaged upon the detector 16 without mechanical movement of any of the system components.

As stated above, the system 10 should be calibrated to achieve the best imaging results. In other words, the values stored in the LUT should be values obtained through calibration of the system 10. If the system 10 functioned ideally without any errors, the values needed to generate the voltage levels that cause the x-ray spot 32 to be positioned at the X, Y coordinates (or r, θ coordinates) on the target 24 could simply be calculated and stored in the LUT 63. However, in real life, generally all systems have imperfections or non-idealities that must be taken into consideration. Because of non-idealities in the system 10, some or all of the calculated values need to be offset in order to compensate for the non-idealities in the system 10. Therefore, the values stored in the LUT 63 are offset values that have been generated during calibration of the system 10 to produce voltages that will cause the x-ray spot 32 to be located in the proper imaging positions.

In the past, calibration has been performed for each circle using empirical data obtained for each circle during calibration. Also, in systems that have actually been implemented, calibration has only been performed for on-axis scanning. As stated above, on-axis laminography only requires a relatively small number of circular scan patterns, i.e., one per each distinct level of magnification (typically 4 in current implementations). However, when off-axis laminography is performed, the number of scan circles that must be generated to cover the object area increases significantly because multiple scan circles for each magnification should be defined. Therefore, using empirical data to calibrate each circle would be extremely time consuming, probably prohibitively so.

Figure 5:
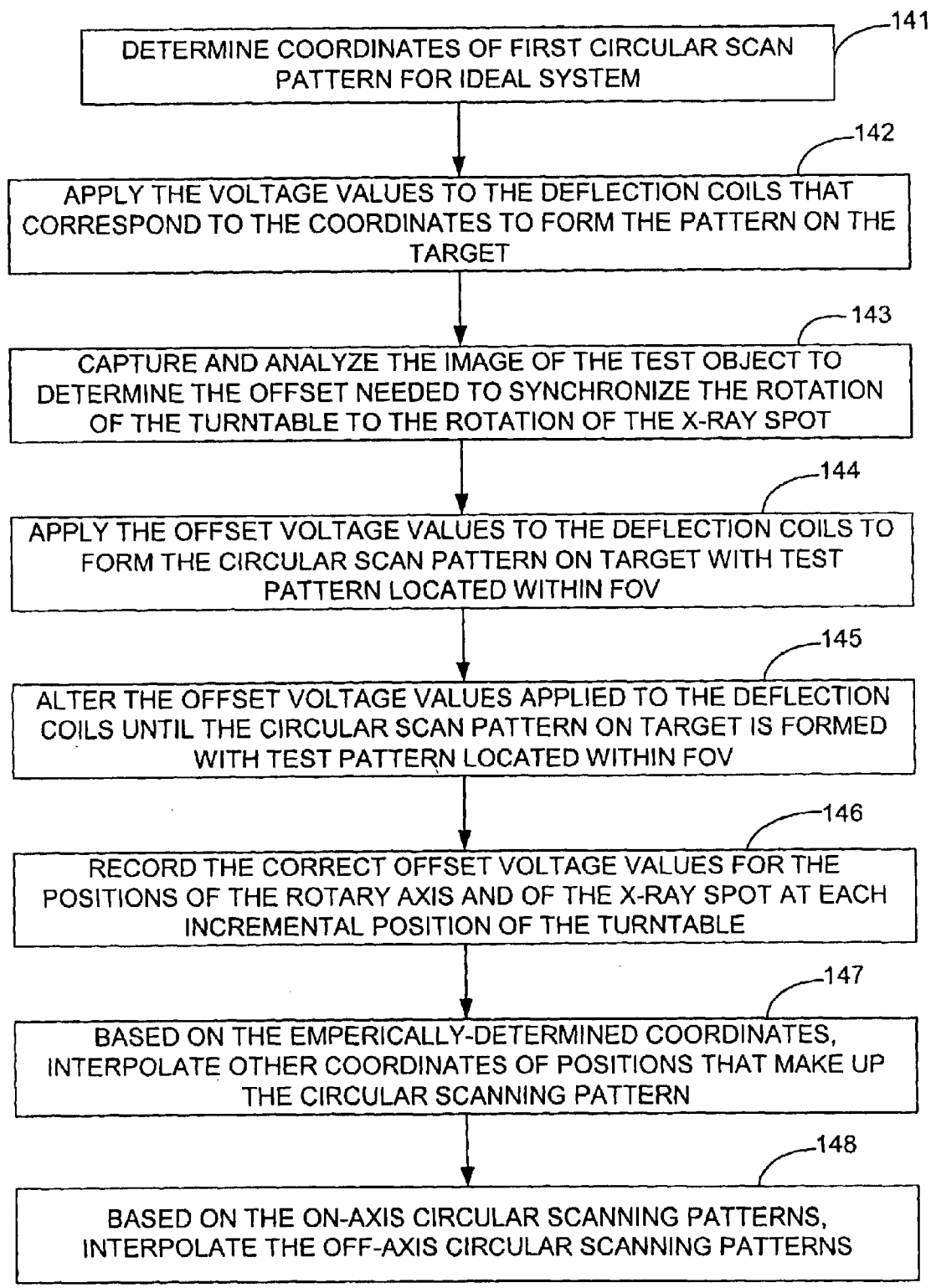
FIG. 5 is a flow chart illustrating the method of the present invention in accordance with an embodiment.

In accordance with the present invention, a calibration technique for off-axis scanning has been developed. The calibration technique of the present invention does not require the gathering of empirical data for each circle. FIG. 5 is a flow chart demonstrating the calibration method of the present invention in accordance with an example embodiment. First, for the first scan circle, X, Y coordinates corresponding to the ideal voltage values (i.e., assuming no system non-idealities) that would be applied to the coils 60 and 62 to synchronize the movement of the x-ray spot 32 to the rotation of the turntable 46 are calculated, as indicated by block 141. Next, this first circular scan pattern is formed on the target 24 by steering the electron beam 30 in accordance with the applied voltage values that correspond to the X, Y coordinates, which are applied to coils 60 and 62, as indicated by block 142. During this step, the object 14 (FIG. 1), which has known recognizable image features (e.g., a printed circuit board (PCB) with five solder dots arranged in a pattern such as the number 5 on the side of a dice) is placed in a fixed, predetermined location on the platform 48 (FIG. 1), nominally centered on the Z-axis 50.

The image of the test object is then captured by the detector 16 and analyzed by the image analysis system 15 to determine the amount, if any, by which the deflection coil voltage values corresponding to the calculated circular scan pattern should be offset to precisely synchronize the rotation of the turntable 46 to the rotation of the x-ray spot 32. This step, which is represented by block 143, may entail, for example, comparing the captured image of the 5-dot solder pattern with a template of what an image of the 5-dot solder pattern would look like if it were centered within the FOV of the system 10. Next, the offset voltage values are applied to the coils 60 and 62 to cause a circular scan pattern to be formed on the target 24 with the test pattern (e.g., the 5-dot solder pattern) located in the center of the FOV (i.e., in the center of the circular scan pattern). This step is represented by block 144. If the test pattern is not in the center of the FOV, the voltage values applied to the coils 60 and 62 will be offset until the pattern is in the center of the FOV, as indicated by block 145. Once a determination has been made that the test pattern is centered, the offset voltage values corresponding to position of the rotary axis of the turntable 46 and the respective position of the x-ray spot 32 will be recorded. This step is represented by block 146.

The rotary axis of the turntable 46 will then be rotated by a certain incremental amount, such as 10°, for example. Again, voltage values will be applied to the coils 60 and 62 until the applied voltage values have caused the test pattern to be located in the center of the FOV for that particular position of the x-ray spot 32 and the associated position of the rotary axis of the turntable 46. When a determination is made that the test pattern is located in the center of the FOV for that particular position of the x-ray spot 32 and the associated position of the rotary axis of the turntable 46, the associated voltage values will be recorded. This is an iterative process that will continue until the rotary axis has rotated 360° in 10° increments and all of the offset voltage values have been recorded for each position of the rotary axis of the turntable 46, as indicated by block 148.

Once the offset coordinates for multiple positions (36 in the above example) of the x-ray spot 32 on the circle have been empirically determined, the locations of other points (e.g., 4,000 points) on the circle that have not been empirically-determined are interpolated, as indicated by block 147. An example of one algorithm that can be used to interpolate the other points on the circle is an algorithm that performs a cubic spline curve-fitting function. Those skilled in the art will understand, in view of the discussion provided herein, the manner in which this and/or other algorithms may be utilized to interpolate points on the circle in between the empirically-determined points.

Steps 141–147 preferably are performed for at least a second circular scan pattern that is concentric with the first circular scan pattern. As will become apparent from the discussion of FIG. 6 below, the preciseness of the interpolated off-axis circular scan patterns increases as the number of on-axis circular scan patterns used to interpolate the off-axis circular scan patterns increases. Therefore, although the calibration technique of the present invention can be determined by using a single on-axis circular scan pattern, preferably more than one on-axis circular scan pattern will be used.

Once a sufficient amount of empirical data has been obtained to generate a sufficient number of on-axis circular scan patterns, the coordinates of off-axis circular scan patterns are obtained using the offset error values empirically determined for the coordinates of the on-axis circular scan patterns, as indicated by block 148. A variety of algorithms are suitable for interpolating the offset error values needed to produce the interpolated off-axis circular patterns. For example, known algorithms such as, the nearest-neighbor algorithm, linear interpolation algorithms, polynomial curve-fitting algorithms, complex curve-fitting algorithms, or a combination thereof, are suitable for interpolating the off-axis circular scan patterns. Because these algorithms can be performed very quickly by a computer, such as, for example, a microprocessor programmed to execute one or more of these algorithms, the calibration time can be greatly reduced in comparison to the amount of time that would be required to empirically generate a large number of circular scan patterns. Therefore, in accordance with the present invention, it is not necessary to obtain a large amount of empirical data in order to perform the calibration method of the present invention, which enables off-axis x-ray laminography to be performed very quickly and with great precision.

Figure 6:
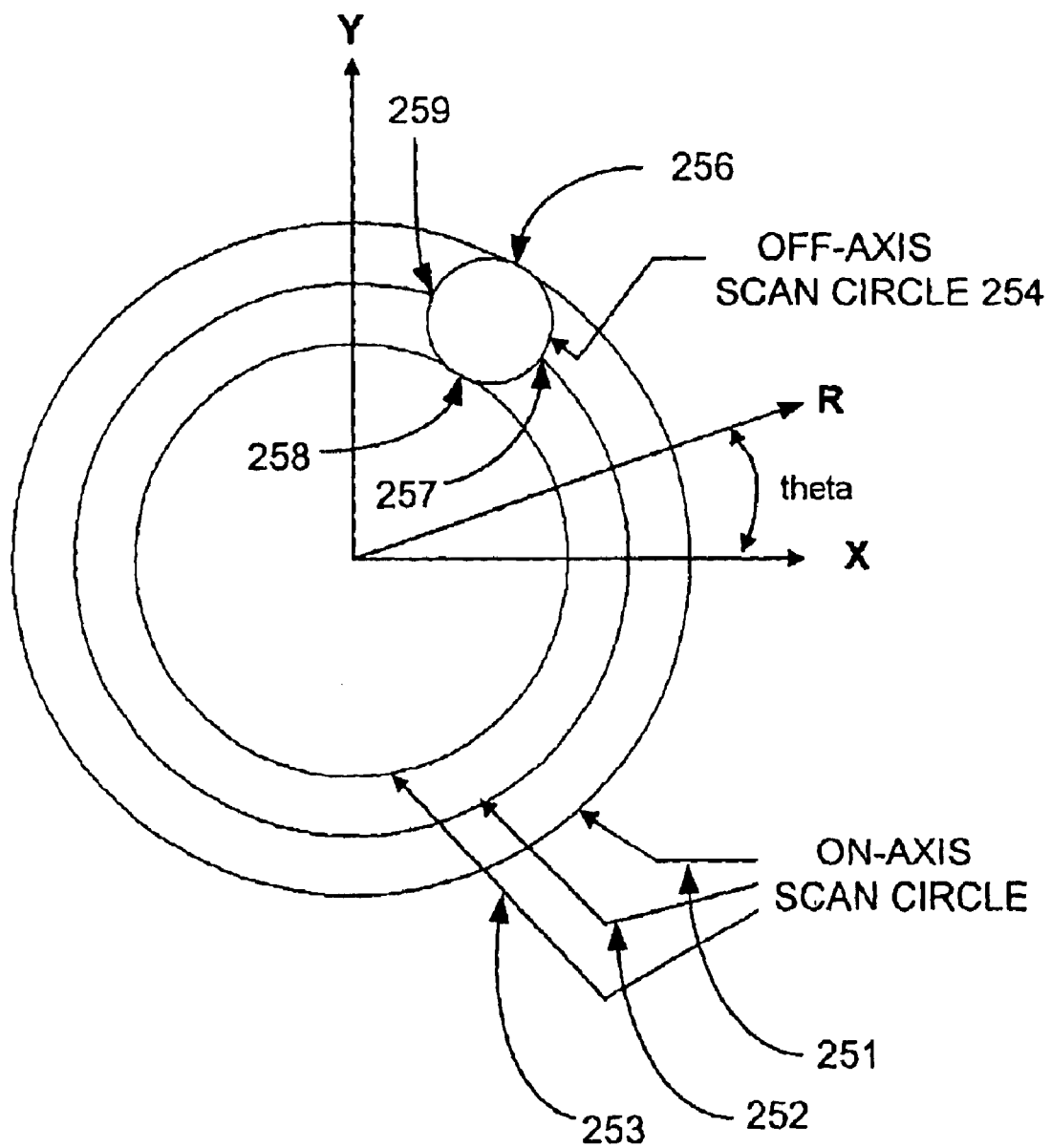
FIG. 6 is a diagram showing the relationship between on-axis, empirically-generated circular x-ray scanning patterns and analytically-derived off-axis circular x-ray scanning patterns.
Figure 7:
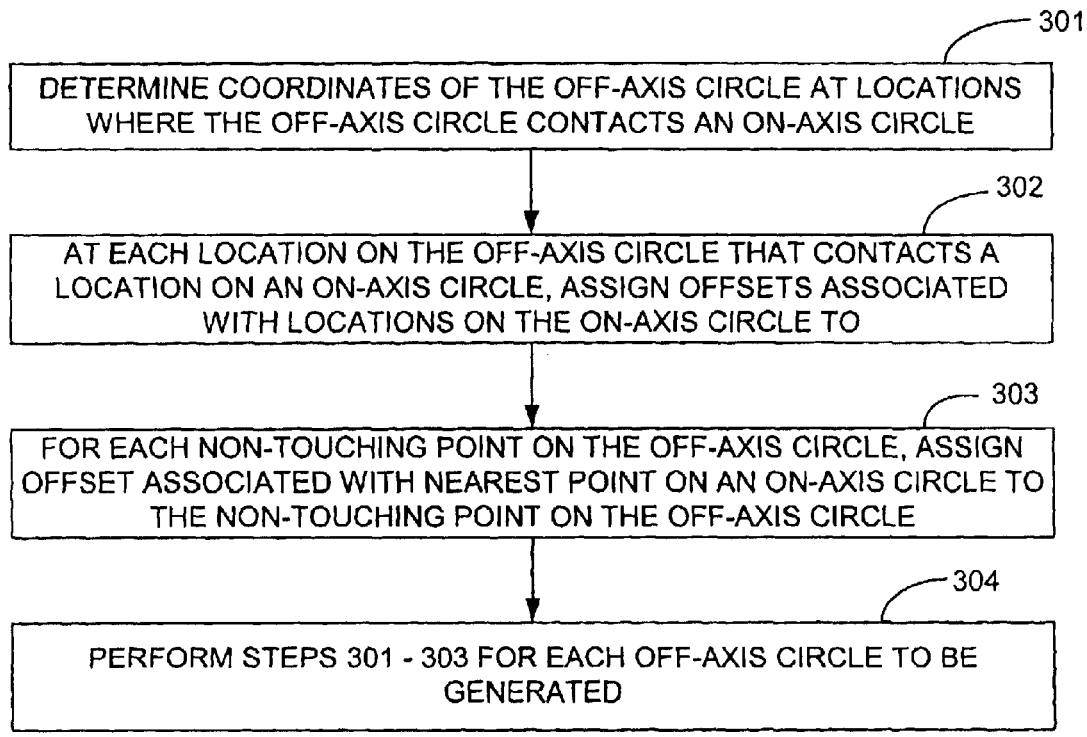
FIG. 7 is a flow chart demonstrating an example embodiment of an interpolation method that can be utilized to analytically derive the off-axis circular scanning patterns from empirically-generated on-axis circular scanning patterns.

An example of the manner in which the nearest-neighbor algorithm can be used to interpolate the offset coordinate values of off-axis circular scan patterns will now be discussed with reference to FIGS. 6 and 7. FIG. 6 is a graphical diagram illustrating three on-axis circles 251, 252 and 253 and one off-axis circle 254. FIG. 7 is a flow chart illustrating the method for interpolating the coordinates of the off-axis circle 254 shown in FIG. 6. Once offsets to polar coordinates (θ, R) of the three on-axis circles 251, 252 and 253 have been empirically determined in the manner discussed above with reference to FIG. 5, the offsets are used to generate offset polar coordinates (θ, R±Δr), where θ is the angle between the X-axis and the point on the circumference of the circle where a line drawn from the origin of the graph intersects that point, where R is the radius of the circle at a point on its circumference, where Δr is the change in the radius R of the circle at a point on its circumference, and where R±Δr is the change in the radius R of the circle at a point on the circumference of the circle as a function of θ.

Preferably, enough empirical data is gathered to enable a sufficient number of concentric on-axis circles, such as circles 251, 252 and 253, to be traced. Once the offsets to the coordinate values for the on-axis circles 251, 252 and 253 have been empirically determined, the offsets to the polar coordinates for off-axis circle 254 (and other off-axis circles) can be interpolated. As shown in FIG. 6, off-axis circle 254 is tangent to on-axis circle 251 at point 256, intersects on-axis circle 252 at points 257 and 259, and is tangent to on-axis circle 253 and point 258. Using the nearest neighbor algorithm, it is assumed that the offsets to the polar coordinates of off-axis circle 254 at intersections 257 and 259 are the same as the offsets to the polar coordinates of on-axis circle 252 at intersections 257 and 259. Likewise, it is assumed that the offsets to the polar coordinates of off-axis circle 254 at locations 256 and 258 are the same as the offsets to the polar coordinates of on-axis circles 251 and 253, respectively.

Therefore, once the off-axis circle 254 has been traced as a perfectly symmetric circle, the coordinate values of the off-axis circle 254 at locations where it touches one of the on-axis circles 251–253 are determined, as indicated by block 301 in FIG. 7. Then, for each point on the off-axis circle 254 that touches a point on one of the on-axis circles 251–253, the offset(s) associated with the coordinates of that point on the on-axis circle is assigned to the point that it touches on the off-axis circle 254. This step is represented by block 302. Once of the offsets of the coordinates of the points on the off-axis circle 254 that touch points on one of the on-axis circles 351, 252 and 253 have been assigned, then offsets are assigned to points on the off-axis circle 254 that do not touch any points on any of the on-axis circles 251–253, as indicated by block 303. This is accomplished as follows. For each point on the off-axis circle 254 that does not touch a point on one of the on-axis circles, a determination is made as to which point on any one of the on-axis circles 251–253 is nearest to point under consideration on the off-axis circle 254. This step is represented by block 304. Once this determination is made, the point on the off-axis circle 254 that is under consideration is assigned the offset of the point it is nearest to on any one of the on-axis circles 251–253. Steps 301–303 are performed for each off-axis circular scan pattern to be generated, as indicated by block 304.

The nearest neighbor algorithm assumes that the offset in a particular region will likely remain substantially constant. Under this assumption, the offset of the nearest neighbor is likely to be the best choice. However, other algorithms such as curve-fitting algorithms may also be used for this purpose (e.g., the aforementioned cubic spline algorithm, least squares algorithms, etc). Those skilled in the art will understand in view of the present disclosure that the present invention is not limited with respect to the interpolation technique used to obtain the coordinates of the off-axis scan circles.

It should also be noted that, in addition to calibrating the system to ensure that the offset values applied to the voltages that control the X, Y coordinates of the spots are correct, it is also important to calibrate the system to ensure that offset values are determined that are applied to the voltage that controls a focus coil (not shown), which, in turn, would control size of the x-ray spots. The system 10 shown in FIG. 1 only illustrates X and Y deflection coils 60 and 62, which are controlled by two separate outputs of the LUT 63. Preferably, the system 10 also comprises a focus coil that controls the spot size. Accordingly, the LUT 63 preferably has three inputs instead of two and three outputs instead of two. Proper adjustment of the focus coil voltage essentially depends on how far the electron beam must travel from the electron gun 18 (FIG. 1) to the target 24. Spot size generally is not an issue when performing on-axis scanning and a fixed voltage can used to provide the best spot size due to the radial symmetry of the spot positions with respect the position of the electron beam gun 18. However, this symmetry does not exist in the off-axis case, and so the focus coil current should be changed dynamically (i.e., modulated) as the electron beam traces out the off-axis scan circle on the target 24.

Providing the ability to control the x-ray spot size enables image resolution to be optimized. Empirical data associated with the size of a given spot of an off-axis trace can be gathered from the relationship between the deflection angle of the electron beam and the focus coil current associated with the spot. Because the desired spot sizes are known based on the spot sizes in the on-axis case, the voltage values used to control the focus coil can be offset by the appropriate amount. Once this has been done empirically for one or more off-axis circles, the focus coil voltage offsets for all of the off-axis circles to be traced can be analytically determined since the focus coil current and the deflection angle will be known in advance for each off-axis circle to be traced. These offset voltage values would be stored in the LUT 63 as a third set of values, the other two sets being for the X and Y deflection coils 60 and 62. Thus, the LUT 63 would have three outputs, one for each coil.

Figure 8:
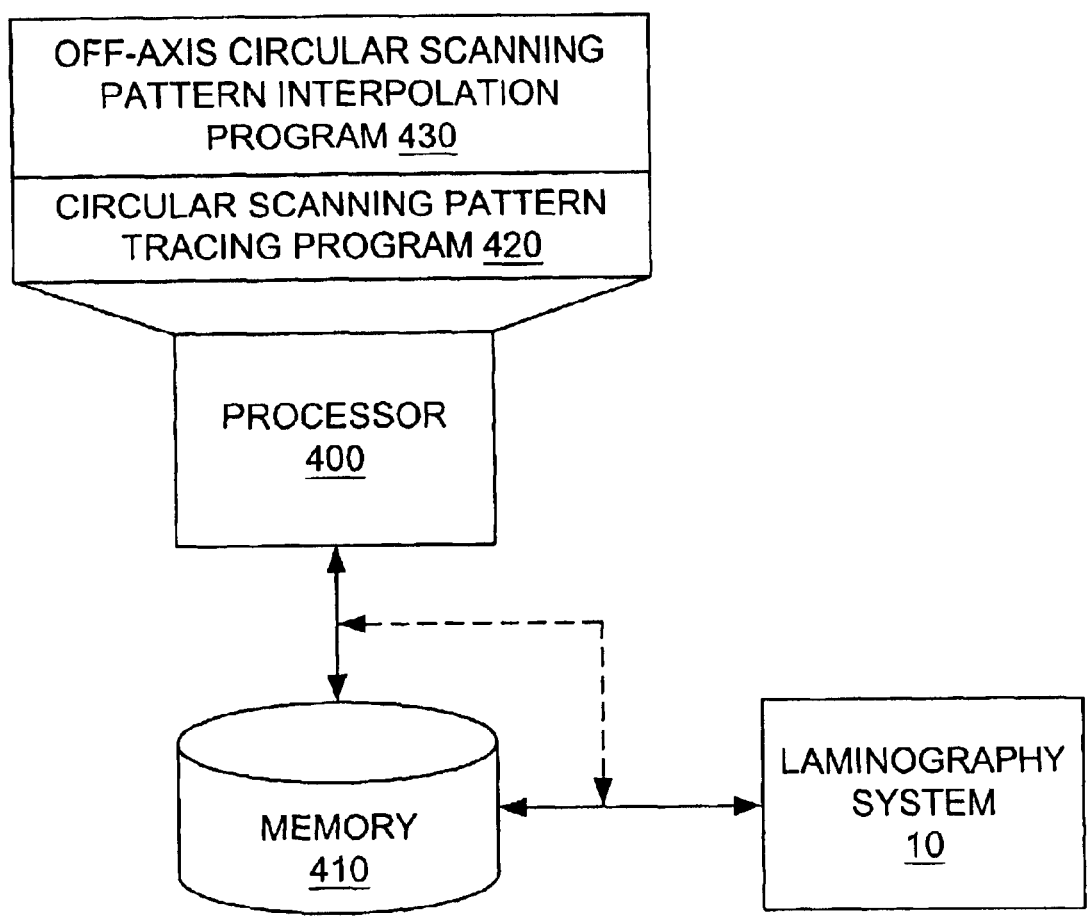
FIG. 8 is a block diagram of an example embodiment of the apparatus of the present invention.

FIG. 8 illustrates a block diagram of the apparatus of the present invention in accordance with an example embodiment. The apparatus shown in FIG. 10 comprises a processor 400 and a memory device 410. The apparatus may be viewed as being part of the laminography system 10 or separate from the laminography system 10, but in communication with it. The memory element 410 may be viewed as including the LUT 63 or as being separate from the LUT 63. The processor 400 may be any type of computational device capable of performing the functions described above with reference to the block diagrams of FIGS. 5 and 7. The processor 400 may also control the operations of the laminography system 10, as indicated by the dashed arrow, or the laminography system 10 may comprise a separate controller for controlling its operations.

Preferably, the processor 400 executes one or more software programs that enable it to perform the functions set forth in FIGS. 5 and 7. For example, a first software program 420 performs the functions of tracing the on-axis ideal circular scanning patterns, empirically determining the offsets for the on-axis circular scanning patterns, interpolating the points on the offset patterns that were not empirically determined, and storing the on-axis offset circular scanning patterns in memory element 410. In accordance with this example, a second software program 430 utilizes the data generated by the first software program 420, which is stored in memory element 410, to perform the functions described above with reference to the flow charts illustrated in FIGS. 5 and 7 and to store the corresponding voltage values in the LUT 63. Of course, the apparatus shown in FIG. 10 is merely one of many possible configurations that can be used to perform the functions of the present invention. Those skilled in the art will understand, in view of the present disclosure, the manner in which different configurations can be created to perform the aforementioned functions. For example, many of the functions can be performed entirely in hardware, rather than by a processor executing software.

Obviating the need to rely solely on data collected empirically to calibrate the x-ray laminography scanning system has advantages other than accelerating the calibration process. For example, the many complex mechanical, optical, magnetic, and electronic components of such a system do not need to be manufactured or adjusted to tight tolerances. They may instead be manufactured to relatively wide tolerances and then characterized as a group. This reduces manufacturing costs and reduces the amount of time to make the system available of the market. The use of some empirical data is advantageous because it compensates for the action of external forces, such as the Earth's magnetic field, for example. The speed at which the calibration process can be performed, due in large part to the fact that the need for empirical data to perform the calibration process is limited, enables the calibration process to be performed quickly. Depending on the balance of resources available between memory and computation, all of the desired off-axis scan circles may be calculated well in advance of their required usage, e.g., during an off-line calibration, or the scan circles may be calculated on-demand during the real-time inspection sequence.

It should be noted that the present invention has been described only with reference to preferred embodiments for example purposes and in the interest of brevity, and that the present invention is not limited to these embodiments. Those skilled in the art will understand, in view of the present disclosure, the manner in which embodiments not disclosed herein can be developed by utilizing the principles and concepts of the present invention. These undisclosed embodiments are also within the scope of the present invention. Those skilled in the art will also understand that modifications can be made to the embodiments discussed herein and that all such modifications are within the scope of the present invention.

What is claimed is:

1. An x-ray laminography imaging system comprising:

a stationary x-ray source;

a target anode;

an x-ray detector, the x-ray source generating a moving pattern of x-ray spots on the target anode synchronously with rotation of the x-ray detector to reduce or eliminate the need to move an object being imaged by the system;

first logic configured to gather empirical calibration data generated during physical calibration of the system during which the stationary x-ray source generates a moving pattern of x-ray spots on the target anode synchronously with rotation of the x-ray detector, the empirical data corresponding to offsets to locations at which the x-ray spots of an on-axis x-ray spot pattern are formed on the target anode;

second logic configured to analytically derive calibration data from the empirical data, the analytically-derived calibration data corresponding to offsets to locations at which x-ray spots of an off-axis x-ray spot pattern are formed on the target anode; and third logic configured to calibrate the system using the empirical data and the analytically-derived calibration data.

2. The system of claim 1, wherein the first, second and third logic correspond to a processor executing a calibration program.

3. An x-ray laminography imaging system comprising:

a stationary x-ray source;

a target anode;

an x-ray detector, the x-ray source generating a moving pattern of x-ray spots on the target anode synchronously with rotation of the x-ray detector to reduce or eliminate the need to move an object being imaged by the system;

a processor, the processor generating control signals and causing said control signals to be delivered to a controllable deflection yoke, the controllable deflection yoke controlling particular locations on the target anode upon which x-rays projected by the x-ray source along a Z-axis impinge, the target anode oriented substantially parallel to a plane that is substantially orthogonal to the Z-axis, the x-rays projected along the Z-axis impinging at particular locations on said target anode, said locations being dependent on control signals received by the controllable deflection yoke that cause the deflection yoke to direct x-rays onto said particular locations on the target anode to form substantially circular x-ray spot patterns on the target anode, each x-ray spot pattern being produced by movement of an x-ray spot in a substantially circular pattern, each x-ray spot corresponding to a beam of x-rays impinging on one of said particular locations on the target anode, the control signals causing the deflection yoke to form at least one substantially circular on-axis x-ray spot pattern on said target anode about the Z-axis and to form at least one substantially circular off-axis x-ray spot pattern on the target anode about an axis that is substantially parallel to the Z-axis, and wherein the processor determines the control signals needed to be delivered to the deflection yoke to cause said at least one off-axis x-ray spot pattern to be formed based on data associated with said at least one on-axis x-ray spot pattern.

4. The system of claim 3, wherein the control signals delivered to the deflection yoke cause at least two substantially circular on-axis x-ray spot patterns to be formed on the target anode about the Z-axis, and wherein the processor determines said at least one substantially circular off-axis x-ray spot pattern from data used by the processor to form said at least two substantially circular on-axis spot patterns.

5. The system of claim 3, wherein the control signals are voltage values and wherein the deflection yoke comprises an X-deflection coil and a Y-deflection coil, said plane being an X, Y plane, each particular location on the target anode corresponding to an X, Y coordinate pair, and wherein voltage values delivered to the X-deflection coil cause the X-deflection coil to direct x-rays in an X-direction, and wherein voltage values delivered to the Y-deflection coil cause the Y-deflection coil to direct x-rays in a Y-direction.

6. The system of claim 3, wherein said at least one on-axis substantially circular x-ray spot pattern is determined by the processor at least partially based on empirical data and wherein said at least one substantially circular off-axis x-ray spot pattern is interpolated by the processor from said at least one on-axis substantially circular x-ray spot pattern.

7. The system of claim 3, wherein said at least one on-axis substantially circular x-ray spot pattern is produced by moving the x-ray spot in a circular pattern over the target anode about the Z-axis in an X, Y plane that is orthogonal to the Z-axis, the movement of the location of the x-ray spot being based on the control signals delivered to the deflection yoke, and wherein the control signals are sinusoidal, each of the sinusoidal signals having a magnitude that dictates the Z-coordinate of an X, Y plane within the object that is imaged by the system.

8. The system of claim 6, wherein said at least one on-axis substantially circular x-ray spot pattern comprises first and second sets of x-ray spots, the first set of x-ray spots being determined empirically by the processor through physical calibration of the system during which the detector and the on-axis substantially circular x-ray spot pattern are synchronously rotated and offsets are determined for each x-ray spot of the first set to form a first set of offset x-ray spots, and wherein once the offsets of said first set of x-ray spots have been empirically determined, the x-ray spots of the second set are interpolated by the processor from the offset first set of x-ray spots.

9. The system of claim 8, wherein once said at least one on-axis substantially circular x-ray spot pattern comprising the first and second sets of x-ray spots has been determined by the processor, said at least one off-axis substantially circular x-ray spot pattern is determined by the processor by interpolating the x-ray spots of the off-axis substantially circular x-ray spot pattern from the on-axis substantially circular x-ray spot pattern, the processor interpolating the off-axis x-ray spots by assigning each off-axis x-ray spot the offset associated with a respective on-axis x-ray spot.

10. The system of claim 9, wherein the processor interpolates the second set of x-ray spots from the first set of x-ray spots by performing a curve-fitting algorithm that uses the first set of x-ray spots to interpolate locations on the target anode of the second set of x-ray spots.

11. The system of claim 9, wherein the processor interpolates the off-axis x-ray spots by executing a curve fitting algorithm that assigns each off-axis x-ray spot the offset associated with a respective on-axis x-ray spot.

12. The system of claim 9, wherein the processor interpolates the off-axis x-ray spots by executing a nearest-neighbor algorithm that assigns each off-axis x-ray spot the offset associated with the on-axis x-ray spot that is nearest to the off-axis x-ray spot.

13. The system of claim 10, wherein the curve fitting algorithm that uses the first set of x-ray spots to interpolate locations on the target of the second set of x-ray spots is a cubic spline algorithm.

14. An apparatus for calibrating an x-ray laminography imaging system, the system utilizing a stationary x-ray source, a rotatably mounted detector, and generating a moving pattern of x-ray spots on a target anode to reduce or eliminate the need to move an object being imaged, the apparatus comprising:

a stationary x-ray source;

a target anode;

an x-ray detector, the x-ray source generating a moving pattern of x-ray spots on the target anode synchronously with rotation of the x-ray detector to reduce or eliminate the need to move an object being imaged by the system;

first logic, the first logic determining control signals needed to be delivered to a deflection yoke to cause at least one substantially circular on-axis x-ray spot pattern to be formed on the target anode about a Z-axis to simulate rotation of the x-ray source, the target anode lying in an X, Y plane that is substantially orthogonal to the Z-axis, each spot of the x-ray spot pattern formed on the target anode having an X-coordinate and a Y-coordinate;

second logic, the second logic processing data to determine offsets to the X, Y coordinates of the x-ray spots of the pattern on the target anode, wherein the data is gathered through calibration of the system as a rotating x-ray detector is synchronized to the motion of the x-ray spots about the Z-axis that form the on-axis x-ray spot pattern;

third logic, the third logic using the offsets to offset the X, Y coordinates of the x-ray spots of the on-axis x-ray spot pattern as they x-ray spot pattern is being formed on the target anode, thereby causing an offset on-axis x-ray spot pattern to be formed on the target anode about the Z-axis; and fourth logic, the fourth logic using the x-ray spot offsets associated with the on-axis x-ray spot pattern to determine a substantially circular off-axis x-ray spot pattern to be formed on the target anode about an axis that is substantially parallel to the Z-axis.

15. The apparatus of claim 14, further comprising:
   fifth logic, the fifth logic generating control signals to be delivered to a deflection yoke, the control signals corresponding to voltage values that have been offset in accordance with the x-ray spot offsets; and
   sixth logic, the sixth logic causing the control signals to be delivered to the deflection yoke, wherein the delivery of the control signals to the deflection yoke causes the offset on-axis x-ray spot pattern to be formed on the target anode about the Z-axis and causes said at least one substantially circular off-axis x-ray spot pattern to be formed on the target anode about an axis that is parallel to the Z-axis.

16. The apparatus of claim 15, wherein the deflection yoke comprises an X-deflection coil and a Y-deflection coil, and wherein voltage values delivered to the X-deflection coil cause the X-deflection coil to deflect x-rays away from the Z-axis in an X-direction, and wherein voltage values delivered to the Y-deflection coil cause the Y-deflection coil to deflect x-rays away from the Z-axis in a Y-direction, and wherein the deflection of the x-rays in the X and Y-directions causes the x-ray spots to be formed at particular X, Y coordinate locations on the target anode.

17. The apparatus of claim 15, wherein the third logic determines the on-axis substantially circular x-ray spot pattern at least partially based on empirical data and wherein said at least one substantially circular off-axis x-ray spot pattern is interpolated by the fourth logic from the offset on-axis substantially circular x-ray spot pattern determined by the third logic.

18. The apparatus of claim 15, wherein the control signals are sinusoidal, each of the sinusoidal signals having a magnitude that dictates a location along the Z-axis of the X, Y plane.

19. The apparatus of claim 14, wherein the offset on-axis substantially circular x-ray spot pattern comprises first and second sets of x-ray spots, the first set of x-ray spots being determined empirically by the third logic from data gathered through physical calibration of the system during which the detector is rotated synchronously with the motion of x-ray spots of the on-axis substantially circular x-ray spot pattern and offsets to the X, Y coordinates of the x-ray spots of the on-axis x-ray spot pattern are determined for each x-ray spot of the first set, and wherein once the offsets to the X, Y coordinates of the first set of x-ray spots have been empirically determined, the third logic interpolates X, Y coordinates of x-ray spots of the second set from the offsets to the X, Y coordinates of the first set.

20. The apparatus of claim 19, wherein once the x-ray spot pattern comprising the first and second sets of x-ray spots has been determined by the third logic, the off-axis substantially circular x-ray spot pattern is determined by the fourth logic from the offset x-ray spots of the on-axis substantially circular x-ray spot pattern by offsetting the X, Y coordinates of each x-ray spot of the off-axis x-ray spot pattern by an amount equal to the offset of respective X, Y coordinates of a respective x-ray spot of the offset on-axis x-ray spot pattern.

21. The apparatus of claim 19, wherein the third logic interpolates the X, Y coordinates of the second set of x-ray spots from the X, Y coordinates of the first set of x-ray spots by performing a curve-fitting algorithm that uses the first set of x-ray spots to interpolate X, Y coordinate locations on the target anode of the second set of x-ray spots.

22. The apparatus of claim 19, wherein the fourth logic interpolates the X, Y coordinates of the off-axis x-ray spots by executing a curve fitting algorithm that utilizes the offset X, Y coordinates of the x-ray spots of the offset on-axis x-ray spot pattern.

23. The apparatus of claim 19, wherein the fourth logic interpolates the X, Y coordinates of the x-ray spots of the off-axis x-ray spot pattern by performing a nearest-neighbor algorithm that assigns the X, Y coordinates of each off-axis x-ray spot the offset associated with the X, Y coordinates of the on-axis x-ray spot that is nearest to the respective off-axis x-ray spot on the target anode.

24. A method for calibrating an x-ray laminography imaging system, the system utilizing a stationary x-ray source, a rotatably mounted detector, and generating a moving pattern of x-ray spots on a target anode to reduce or eliminate the need to move an object being imaged, the method comprising the steps of:
   determining control signals needed to be delivered to a deflection yoke to cause at least one substantially circular on-axis x-ray spot pattern to be formed on a target anode about a Z-axis to simulate rotation of an x-ray source, the target anode lying in an X, Y plane that is substantially orthogonal to the Z-axis, each spot of the x-ray spot pattern formed on the target anode having an X-coordinate and a Y-coordinate;
   processing data to determine offsets to the X, Y coordinates of the x-ray spots of the pattern on the target anode, wherein the data is gathered through calibration of the system as a rotating x-ray detector is synchronized to the motion of the x-ray spots about the Z-axis that form the on-axis x-ray spot pattern;
   using the offsets to offset the X, Y coordinates of the x-ray spots of the on-axis x-ray spot pattern as they x-ray spot pattern is being formed on the target anode, thereby causing an offset on-axis x-ray spot pattern to be formed on the target anode about the Z-axis; and
   using the x-ray spot offsets associated with the on-axis x-ray spot pattern to determine a substantially circular off-axis x-ray spot pattern to be formed on the target anode about an axis that is substantially parallel to the Z-axis.

25. The method of claim 24, further comprising:
   generating the offset control signals to be delivered to a deflection yoke, the offset control signals corresponding to voltage values that have been offset in accordance with the x-ray spot offsets; and
   causing the offset control signals to be delivered to the deflection yoke, wherein the delivery of the offset control signals to the deflection yoke causes the offset on-axis x-ray spot pattern to be formed on the target anode about the Z-axis and causes said at least one substantially circular off-axis x-ray spot pattern to be formed on the target anode about an axis that is parallel to the Z-axis.

26. The method of claim 25, wherein the deflection yoke comprises an X-deflection coil and a Y-deflection coil, and wherein voltage values delivered to the X-deflection coil cause the X-deflection coil to deflect x-rays away from the Z-axis in an X-direction, and wherein voltage values delivered to the Y-deflection coil cause the Y-deflection coil to deflect x-rays away from the Z-axis in a Y-direction, and wherein the deflection of the x-rays in the X and Y-directions causes the x-ray spots to be formed at particular X, Y coordinate locations on the target anode.

27. The method of claim 25, wherein the determination of the on-axis substantially circular x-ray spot pattern is based at least partially on empirical data and wherein said at least one substantially circular off-axis x-ray spot pattern is interpolated from the offset on-axis substantially circular x-ray spot pattern.

28. The method of claim 26, wherein the control signals are sinusoidal, each of the sinusoidal signals having a magnitude that dictates a location along the Z-axis of the X, Y plane.

29. The method of claim 24, wherein the offset on-axis substantially circular x-ray spot pattern comprises first and second sets of x-ray spots, the first set of x-ray spots being determined empirically from data gathered through physical calibration of the system during which the detector is rotated synchronously with the motion of x-ray spots of the on-axis substantially circular x-ray spot pattern, and wherein offsets to the X, Y coordinates of the x-ray spots of the on-axis x-ray spot pattern are determined for each x-ray spot of the first set, and wherein once the offsets to the X, Y coordinates of the first set of x-ray spots have been empirically determined, the X, Y coordinates of x-ray spots of the second set are interpolated from the offsets to the X, Y coordinates of the first set.

30. The method of claim 29, wherein once the x-ray spot pattern comprising the first and second sets of x-ray spots has been determined, the off-axis substantially circular x-ray spot pattern is determined from the offset x-ray spots of the on-axis substantially circular x-ray spot pattern by offsetting the X, Y coordinates of each x-ray spot of the off-axis x-ray spot pattern by an amount equal to the offset of respective X, Y coordinates of a respective x-ray spot of the offset on-axis x-ray spot pattern.

31. The method of claim 29, wherein the X, Y coordinates of the second set of x-ray spots are interpolated from the X, Y coordinates of the first set of x-ray spots by performing a curve-fitting algorithm that uses the first set of x-ray spots to interpolate X, Y coordinate locations on the target anode of the second set of x-ray spots.

32. The method of claim 29, wherein the X, Y coordinates of the off-axis x-ray spots are interpolated by executing a curve fitting algorithm that utilizes the offset X, Y coordinates of the x-ray spots of the offset on-axis x-ray spot pattern.

33. The method of claim 29, wherein the X, Y coordinates of the x-ray spots of the off-axis x-ray spot pattern are interpolated by performing a nearest-neighbor algorithm that assigns the X, Y coordinates of each off-axis x-ray spot the offset associated with the X, Y coordinates of the on-axis x-ray spot that is nearest to the respective off-axis x-ray spot on the target anode.

34. A computer-readable medium having a computer program embodied thereon for calibrating an x-ray laminography imaging system, the system utilizing a stationary x-ray source, a rotatably mounted detector, and generating a moving pattern of x-ray spots on a target anode to reduce or eliminate the need to move an object being imaged, the computer-readable medium comprising:

a first code segment for determining control signals needed to be delivered to a deflection yoke to cause at least one substantially circular on-axis x-ray spot pattern to be formed on a target anode about a Z-axis to simulate rotation of an x-ray source, the target anode lying in an X, Y plane that is substantially orthogonal to the Z-axis, each spot of the x-ray spot pattern formed on the target anode having an X-coordinate and a Y-coordinate;

a second code segment for processing data to determine offsets to the X, Y coordinates of the x-ray spots of the pattern on the target anode, wherein the data is gathered through calibration of the system as a rotating x-ray detector is synchronized to the motion of the x-ray spots about the Z-axis that form the on-axis x-ray spot pattern;

a third code segment that uses the offsets to offset the X, Y coordinates of the x-ray spots of the on-axis x-ray spot pattern as they x-ray spot pattern is being formed on the target anode, thereby causing an offset on-axis x-ray spot pattern to be formed on the target anode about the Z-axis; and a fourth code segment that uses the x-ray spot offsets associated with the on-axis x-ray spot pattern to determine a substantially circular off-axis x-ray spot pattern to be formed on the target anode about an axis that is substantially parallel to the Z-axis.

* * * * *